United States Patent
Nemoto et al.

(10) Patent No.: US 9,696,330 B2
(45) Date of Patent: Jul. 4, 2017

(54) SAMPLE CONVEYOR APPARATUS AND SPECIMEN TESTING AUTOMATION SYSTEM

(71) Applicant: Hitachi High-Technologies Corporation, Tokyo (JP)

(72) Inventors: Tomoyuki Nemoto, Tokyo (JP); Tatsuya Fukugaki, Tokyo (JP); Naoto Tsujimura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1 day.

(21) Appl. No.: 14/422,716

(22) PCT Filed: Aug. 30, 2013

(86) PCT No.: PCT/JP2013/073417
§ 371 (c)(1),
(2) Date: Feb. 20, 2015

(87) PCT Pub. No.: WO2014/050437
PCT Pub. Date: Apr. 3, 2014

(65) Prior Publication Data
US 2015/0233955 A1    Aug. 20, 2015

(30) Foreign Application Priority Data

Sep. 26, 2012   (JP) ................................ 2012-211651

(51) Int. Cl.
*B65G 15/00*     (2006.01)
*G01N 35/04*     (2006.01)
(Continued)

(52) U.S. Cl.
CPC ............. *G01N 35/04* (2013.01); *B65G 15/22* (2013.01); *B65G 21/2072* (2013.01);
(Continued)

(58) Field of Classification Search
CPC .... B65G 21/10; B65G 15/22; B65G 21/2072; B65G 23/04; B65G 23/44
(Continued)

(56) References Cited

U.S. PATENT DOCUMENTS 3,572,496 A * 3/1971 Cutts ...................... B65G 21/14
                                                          198/837
4,457,422 A * 7/1984 Hurd ...................... B65G 15/14
                                                          198/604
(Continued)

FOREIGN PATENT DOCUMENTS

EP       1889801 A1    2/2008
EP       2485058 A1    8/2012
(Continued)

OTHER PUBLICATIONS

International Search Report in PCT/JP2013/073417, dated Sep. 24, 2013.
(Continued)

*Primary Examiner* — William R Harp
(74) *Attorney, Agent, or Firm* — Mattingly & Malur, PC

(57) ABSTRACT

In a conventional conveyor line, an empty specimen rack conveyor line is provided separately from a specimen rack conveyor line having a specimen mounted thereon. However, crossing of the conveyor lines leads to the decrease in processing speed. Also, when a specimen rack conveyor line and an empty specimen rack conveyor line are configured on two stages, a vertical movement mechanism needs to be added in order to connect the upper-stage conveyor line and the lower-stage conveyor line, and there is a possibility that the system is complicated and the cost thereof is increased. In the present invention, by connecting an empty holder conveyor line and a main conveyor line disposed up and down on two stages via one conveyor line having a horizontal part and an inclined part, crossing of the conveyor lines can be eliminated and an inexpensive structure can be achieved.

8 Claims, 5 Drawing Sheets

(51) Int. Cl.
*B65G 21/20* (2006.01)
*B65G 15/22* (2006.01)
*B65G 23/44* (2006.01)
*B65G 23/04* (2006.01)

(52) U.S. Cl.
CPC ............ *B65G 23/04* (2013.01); *B65G 23/44* (2013.01); *G01N 2035/046* (2013.01); *G01N 2035/0467* (2013.01)

(58) Field of Classification Search
USPC .................. 198/836.2, 836.3, 602, 861.1
See application file for complete search history.

(56) References Cited

U.S. PATENT DOCUMENTS

| | | | | |
|---|---|---|---|---|
| 5,090,550 | A * | 2/1992 | Axmann | B65G 21/10 198/311 |
| 5,875,883 | A * | 3/1999 | Ertel | B65G 15/42 198/821 |
| 6,626,285 | B2 * | 9/2003 | Enomoto | B23Q 11/0057 198/581 |
| 8,074,793 | B2 * | 12/2011 | Jager | B65G 21/06 198/435 |
| 2015/0101910 | A1 * | 4/2015 | Cribiu | B65G 15/26 198/592 |

FOREIGN PATENT DOCUMENTS

| | | |
|---|---|---|
| GB | 828449 A | 2/1960 |
| JP | 2005-156196 | 6/2005 |
| JP | 2007-314328 | 12/2007 |
| JP | 2010-284124 | 12/2010 |

OTHER PUBLICATIONS

Extended European Search Report received in corresponding European Application No. 13842110.2 dated May 2, 2016.

* cited by examiner

SAMPLE CONVEYOR APPARATUS AND SPECIMEN TESTING AUTOMATION SYSTEM

TECHNICAL FIELD

The present invention relates to a conveyor apparatus which conveys a sample or specimen such as blood and a specimen conveyor system including the conveyor apparatus.

BACKGROUND ART

A specimen testing automation system is a system in which various apparatuses such as a specimen pre-processing apparatus and a specimen analyzing apparatus are connected to each other via specimen conveyor lines for automated conveyance of a specimen among the respective apparatuses, and such a specimen testing automation system is introduced to a relatively large-scale facility in many cases. In these large-scale facilities, for performing various tests such as a biochemical test, immunological test, coagulation test, and hematological test, a plurality of specimens are sometimes collected from one patient. For this reason, many holders and specimen racks are required to be loaded to the specimen testing automation system, and spaces for placing and storing them are also required.

In a conventional specimen testing automation system, a specimen rack conveyor line for conveying a specimen rack having a specimen mounted thereon and an empty rack conveyor line for conveying an empty specimen rack are provided. However, due to the structure in which the plurality of lines cross each other, there is a problem of decreasing processing speed.

Patent Document 1 discloses an apparatus in which a specimen supply conveyor line and an empty specimen conveyor line are configured as two-stage lines, that is, an upper-stage conveyor line and a lower-stage conveyor line, and a rotating mechanism with a vertical movement mechanism is disposed between the upper-stage conveyor line and the lower-stage conveyor line, thereby allowing efficient conveyance of a specimen rack and an empty rack.

RELATED ART DOCUMENT

Patent Document

Patent Document 1: Japanese Patent Application Laid-Open Publication No. 2005-156196

SUMMARY OF THE INVENTION

Problems to be Solved by the Invention

In the specimen conveyor apparatus disclosed in Patent Document 1, the vertical movement mechanism or the like needs to be added for the connection between the upper-stage conveyor line and the lower-stage conveyor line. In the vertical movement mechanism, a driving source only for vertical movements needs to be provided separately from the conveyor lines, and the apparatus structure is thus complicated, so that the system cost increases in some cases.

An object of the present invention is to provide an inexpensive specimen testing automation system in which decrease in processing speed due to crossing of conveyor lines does not occur while avoiding the system from being complicated.

Means for Solving the Problems

Features of the present invention are as follows.

A sample conveyor apparatus includes: two or more conveyor paths provided along a conveyor route for conveying a sample; a belt used in common by the conveyor paths; and a driving source which drives the belt, thereby conveying at least any of a sample, a sample holder, and a sample rack mounted on the belt, the two or more conveyor paths are disposed so as to form a predetermined angle, and adjusting means which adjusts an angle of the belt is provided at a connecting part of the conveyor paths.

Effects of the Invention

According to the present invention, it is possible to provide a specimen testing automation system capable of avoiding decrease in processing speed due to crossing of conveyor lines and having an inexpensive structure without increasing the size and complicating the structure of the system.

BRIEF DESCRIPTIONS OF THE DRAWINGS

DETAILED DESCRIPTION OF PREFERRED EMBODIMENTS

In the present embodiment, one example of the structure of a specimen testing automation system obtained by the combination of various modules will be described. In a specimen testing automation system 11, an arbitrary number of various modules such as a loading module, a centrifugal module, an opening module, a specimen dispensing module, a closing module, and a storage module are arranged in an arbitrary structure. Ten or more modules are connected in a large-scale facility in some cases.

Figure 1:
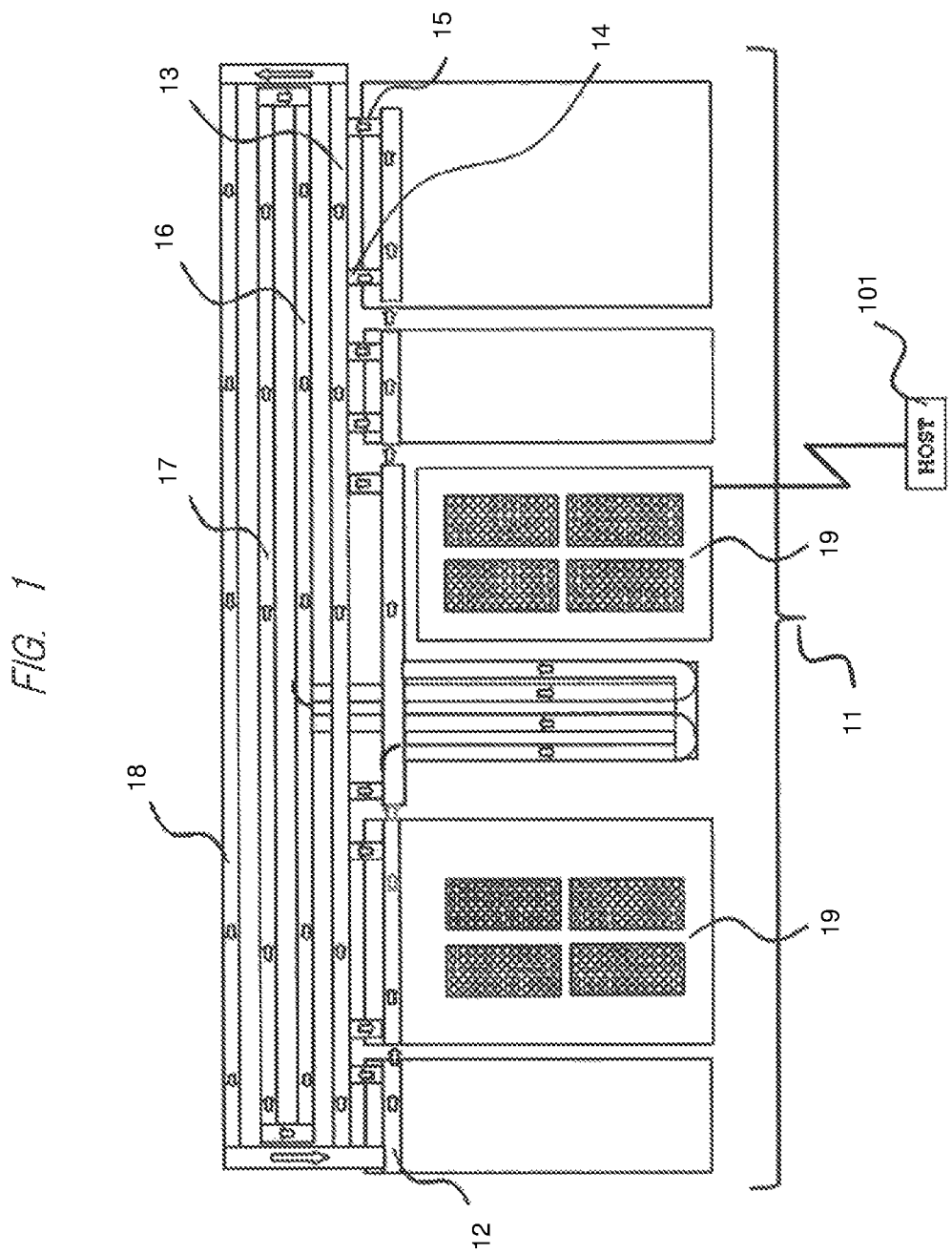
FIG. 1 is a schematic view of a specimen testing automation system according to the present invention.

FIG. 1 is a schematic view showing an example of the specimen testing automation system. Test tubes each containing a specimen and loaded into the system are mounted on test tube holders 31 each having a unique ID number, and are supplied to each module through a conveyor line in the system. As ID identifying means for reading this ID number, for example, barcode readers or tag readers are disposed at various places.

Figure 4:
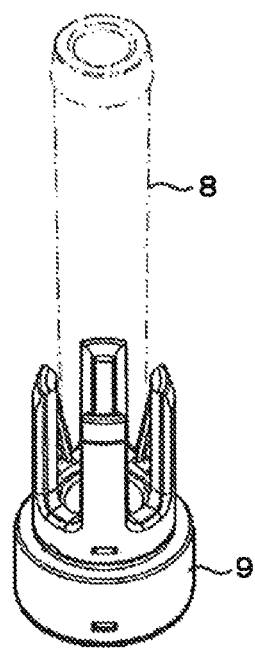
FIG. 4 is a perspective view of a test tube holder, which is an example of a conveyance object in the present invention.
Figure 5:
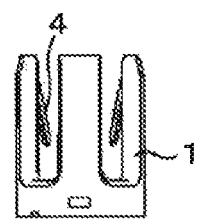
FIG. 5 is a structural diagram of the test tube holder, which is the conveyance object in the present invention.
Figure 5:
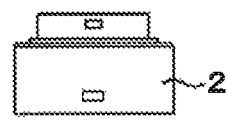
Figure 5:
Figure 5:
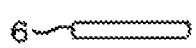
Figure 5:
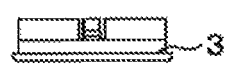

An example of a conveyance object is, for example, a test tube holder 9 shown in FIG. 4 and FIG. 5. This test tube holder 9 can hold one test tube containing a specimen and convey the test tube via a conveyor line to each module. The test tube holder 9 is configured of a housing 1 with a spring for fixing a test tube, a test tube holder body housing 2, and a bottom lid housing 3.

The housing 1 with a spring for fixing a test tube has a columnar structure whose center part is roundly bored so as to allow the insertion of the test tube, and is provided with spring parts 4 inside projecting parts extending upward. Note that the housing 1 with a spring basically has a columnar shape in the present embodiment, but it may have any shape as long as the housing can vertically hold the test tube by the spring parts 4 provided equidistantly or equiangularly, and an outer shape of the housing may be a polygonal column shape.

The test tube holder body housing has a cylindrical shape, and desirably has a cavity part therein. In the cavity part, a tag 6 with a unique ID number, a weight 5 for stably conveying the test tube, and others are housed. Also, the test tube holder body housing and the bottom lid housing have an outer diameter larger than that of the test tube to be conveyed and smaller than the width of the conveyor line. Note that the shape of the test tube holder body housing and the bottom lid housing may be, for example, a polygonal shape. Even in that case, a maximum length in a cross-sectional direction is desirably smaller than the width of the conveyor line.

Next, a specimen flow in the system will be described.

An operator places a tray 19, in which fifty to hundred specimens to be processed can be laid, in a loading module 102 in the specimen testing automation system 11. In the loading module 102, the specimens in the tray 19 are sequentially transferred onto the test tube holders 31 by a test tube chuck mechanism (not shown).

Empty test tube holders 31 are accommodated on an empty holder conveyor line 16. At a tray installation location in the loading module 102, identifying means, which identifies that a tray having specimens mounted thereon has been installed, is provided, and when a new tray is installed, empty holders 31 are sequentially conveyed to the loading module in accordance with a conveyance request from the loading module via communication.

After the specimens are transferred onto the test tube holders 31, barcode information attached to the test tubes in the loading module is read. The read barcode information is forwarded to a host computer 101, and type information of the specimen registered in the host computer 101 is returned to the system.

In the system, based on the returned type information, it is determined which module the specimen is to make a stop at or which module the specimen is to skip. Based on these pieces of information, a specimen conveyor line conveys the specimens mounted on the test tube holders 31 to each module.

The specimens for which all requested processes have been completed are conveyed finally to a storage module 103 in the specimen testing automation system 11, are extracted from the test tube holders 31 by the test tube chuck mechanism (not shown), and are stored in the tray 19. The empty test tube holders 31 after the specimens are extracted are returned to the empty holder conveyor line 16.

The conveyor line in this system is made up of various conveyor lines including a main conveyor line 12, an emergency passing line 13, branch lines 14 and 15, empty holder conveyor lines 16 and 17, and a return line 18.

The main conveyor line 12 is a line for conveying the specimens loaded to the system to each module.

The emergency passing line 13 is a line by which an emergent specimen overtakes a preceding specimen. By letting the specimen pass through this emergency passing line 13, a specimen not required to be processed (for example, specimen not required to be centrifugalized) can skip a stop at a module.

A specimen required to be processed in a predetermined module (for example, specimen required to be dispensed) makes a stop at a specimen dispensing module by using the branch lines 14 and 15 disposed at each module.

The return line 18 is a conveyor line by which specimens loop in the system 11. For example, when the specimen which has once passed through the dispensing module is required to be dispensed again for re-testing or additional testing, the specimen is made to loop in the system 11 by using this return line 18, and is conveyed again to a necessary module.

The empty holder conveyor lines 16 and 17 are provided on a lower stage of a plane which is in parallel with the main conveyor line 12 and on which the main conveyor line 12, the emergency passing line 13, the branch lines 14 and 15, and the return line 18 are provided.

By forming a loop also by the empty holder conveyor lines 16 and 17 in the same manner, empty holders can be accommodated and supplied in flux. Furthermore, the empty holder conveyor lines 16 and 17 desirably have substantially the same line length as those of the main conveyor line 12 and the return line 18. Consequently, it is possible to handle subsequent changes such as addition and reduction of a module, and system extensibility can be enhanced. Specifically, an optimal number of empty holders can be provided in accordance with the scale of the system.

This is because the maximum number of empty holders that are likely to be used in the present system is equal to the number at the time when the line is completely filled with the test tube holders 31. In other words, the test tube holders 31 more than those completely filling the entire line cannot be conveyed and therefore are unnecessary. Due to the nature thereof, the emergency passing line 13 only passes the test tube holder 31 without stopping it, and does not accumulate the holders. Therefore, if a sum of line lengths of the empty holder conveyor lines 16 and 17 is substantially the same as a line length obtained by adding the main conveyor line 12 and the return line 18 together, the maximum number of empty holders to be used in the system can be accommodated in the empty holder conveyor lines 16 and 17. Consequently, an optimal number of empty holders can always be provided in accordance with the scale of the system.

The empty holders accommodated in the empty holder conveyor lines 16 and 17 are supplied via a connecting line 104 to the main conveyor line 12, and also are collected from the main conveyor line 12 to the empty holder conveyor line 16. The connecting line 104 connects the empty holder conveyor line provided on the lower stage and the main conveyor line 12 provided on an upper end via an inclined line. Details of the structure of the inclined line in the present embodiment will be described further below. In the case where the inclination is too steep to stably convey holders when the lower stage and the upper stage are directly connected, a turning mechanism may be provided so that the upper stage and the lower stage are gradually brought closer in distance through repeated turns. In the embodiment of FIG. 1, an example of the connecting line 104 including one turning mechanism is shown.

Figure 2:
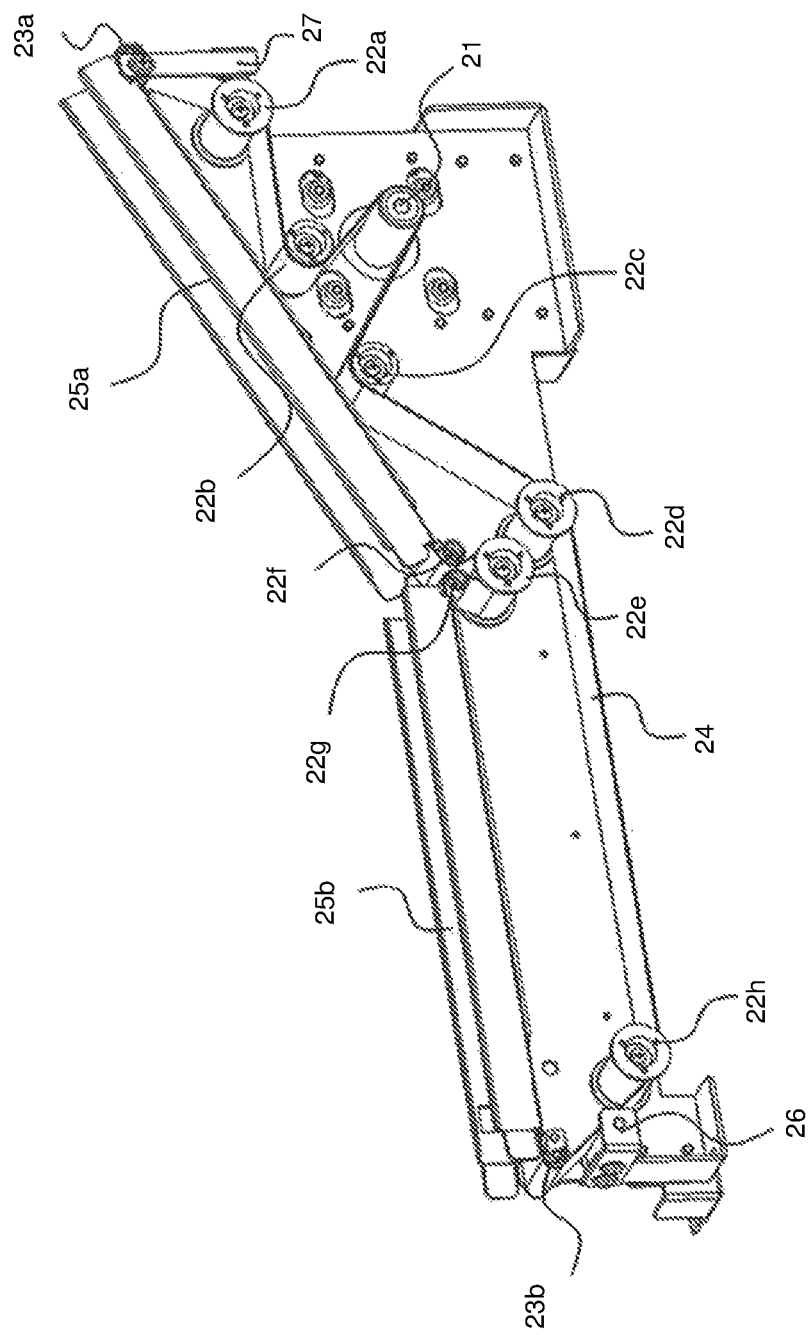
FIG. 2 is a perspective view of a conveyor line having both of a horizontal part and an inclined part according to the present invention.

FIG. 2 is a perspective view showing a bent line having a first conveyor path 28*b* and a second conveyor path 28*a* together as an example of the connecting line 104.

In the bent line, by driving a motor (not shown), one belt 24 wound along a driving pulley 21, driven pulleys 22, and tail pulleys 23 is driven to rotate, thereby moving the holder 31 mounted on an upper surface of the belt 24. Since holder guide rails 25a and 25b are provided on both sides of the line, the holder 31 is prevented from falling down during the line conveyance.

Also, belt tension can be adjusted by adjusting at least one of the positions of the driving pulley 21 and the driven pulleys 22. Furthermore, belt imbalance can be prevented by adjusting at least one of the positions of a meandering prevention pulley 26, a meandering prevention plate 27, and the tail pulleys 23.

In the bent line in the present invention, lines with different inclinations can be connected by using one belt. FIG. 2 shows the bent line in which the first conveyor path 28b having the conveyor line extending substantially horizontally and the second conveyor path 28a having the conveyor line inclined from horizontal at a predetermined angle are connected. Between the first conveyor path 28b and the second conveyor path 28a, three driven pulleys 22e, 22g, and 22f are provided, and by moving the position of the driven pulley 22g or 22f, the angle of a connecting part between the first conveyor path 28b and the second conveyor path 28a can be adjusted. When the belt 24 is driven in a direction of conveying a specimen from the first conveyor path 28b to the second conveyor path 28a, the belt 24 from the first conveyor path 28b crawls into a lower side of the bent line via the driven pulley 22g, and appears on an upper side of the second conveyor path 28a via the driven pulleys 22e and 22f. The belt 24 having passed through the second conveyor path 28a again crawls into the lower side of the bent line via the tail pulley 23a, and is introduced to an entrance portion of the first conveyor path 28b. With this structure, the first conveyor path 28b and the second conveyor path 28a with different inclinations can be connected, and furthermore, the belt can be driven by driving the single driving pulley 21.

Note that the distance between the driven pulley 22g and the driven pulley 22f is desirably half or smaller than the length of a conveyance object in a conveyance direction. For example, when the conveyance object is a test tube holder shown in FIG. 4, the distance between the driven pulley 22g and the driven pulley 22f is desirably half or smaller than the size of the diameter of the bottom surface of the test tube holder body housing. By adjusting the distance between the driven pulleys in this manner, the test tube holder can be stably conveyed.

When conveyor lines are disposed up and down in multiple stages as shown in FIG. 1 of the present embodiment and specimens and holders are required to be mutually conveyed, it is necessary to provide a connecting line for connecting an upper-stage conveyor line and a lower-stage conveyor line. The connecting line mechanism 104 is provided between other mechanisms, and it is often the case that a sufficient space cannot be ensured. In such a case, in a normal conveyor line structure, the upper-stage conveyor line and the lower-stage conveyor line are connected while avoiding the interference with other mechanisms, and therefore the installation location is limited and the structure size is increased in some cases. By contrast, in the bent line of the present invention, since two or more conveyor lines can be connected at any angle, the upper-stage conveyor line and the lower-stage conveyor line can be connected while avoiding surrounding mechanisms, and the entire apparatus can be made compact.

Figure 3:
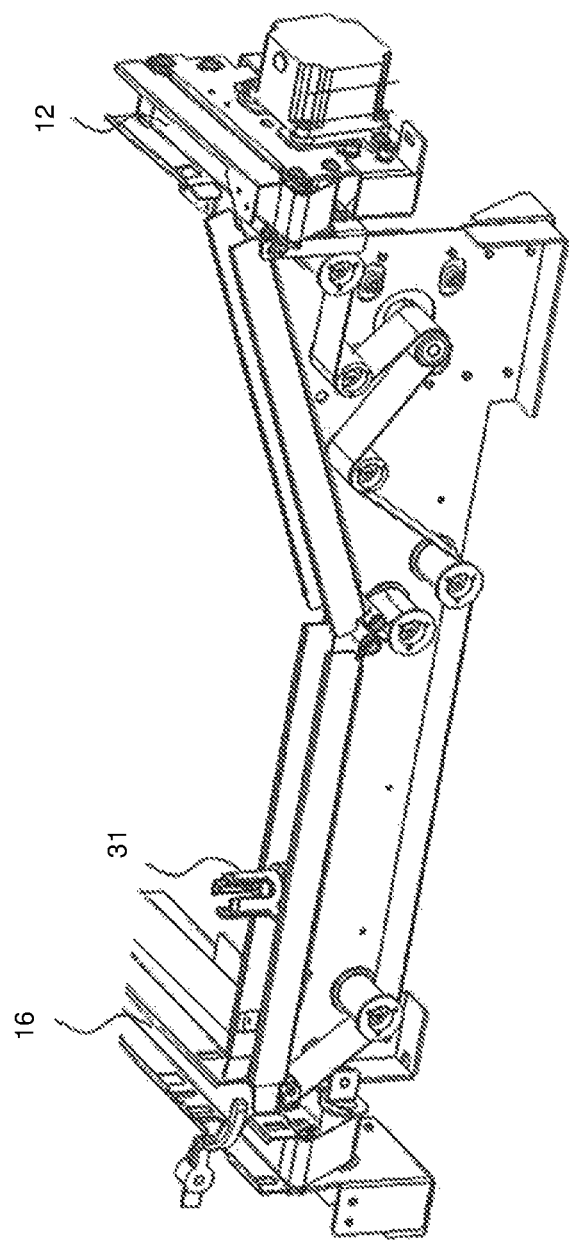
FIG. 3 is a perspective view of a connecting part of two conveyor lines disposed in upper and lower stages according to the present invention.

FIG. 3 is a perspective view of the bent line which connects the empty holder conveyor line 16 and the main conveyor line 12. Here, by way of example, the structure of a connecting line for conveying a holder from the main conveyor line 12 to the empty holder conveyor line is shown.

When all processes are completed, empty holders from which specimens have been extracted in the storage module are conveyed from the main conveyor line 12 via the bent line (connecting line 104) to the empty holder conveyor line 16. Here, the connecting line 104 has a first conveyor path provided substantially horizontally and a second conveyor path provided so as to be inclined at a predetermined angle with respect to the first conveyor path. By connecting the empty holder conveyor line 16 on the lower stage and the main conveyor line 12 on the upper stage by the connecting line 104 having the horizontal first conveyor path and the inclined second conveyor path together, the arrangement of conveyor line is not restricted by the arrangement of surrounding mechanisms. Also, since the first conveyor path provided horizontally and the second conveyor path provided so as to be inclined can be driven by a single driving source (motor), cost reduction of the entire apparatus can be achieved.

Note that, in the present embodiment, the bent line having the first conveyor path provided horizontally and the second conveyor path disposed at a predetermined angle with respect to the first conveyor path has been described as an example, but the present invention is not limited to this embodiment. Since the first conveyor path and the second conveyor path can be connected at any angle, the bent line can be adjusted so as to optimally fit with the arrangement of surrounding mechanisms and conveyance spaces within the range of being able to convey the specimen. Also, one bent line may be configured by connecting three or more lines.

Furthermore, although an example capable of holding only one specimen container has been described as the specimen holder 31 in the present embodiment, the invention of the present application may be a conveyor apparatus which conveys a so-called rack type capable of having a plurality of specimen containers mounted thereon. A typified rack is a five-piece rack capable of conveying five test tubes along a conveyance direction of the conveyor line. In this case, since the rack is longer than the holder, if the angle formed by the first conveyor path and the second conveyor path is large, there is a possibility that the rack is stuck at the connecting part of the conveyor paths and cannot be smoothly conveyed, and thus the angle is required to be optimally adjusted. In this case, the distance between the driven pulley 22g and the driven pulley 22f is desirably half or smaller than the length of the five-piece rack in the conveyance direction as described above, and the distance between the driven pulleys can be made longer than that when the test tube holder is conveyed.

DESCRIPTION OF REFERENCE CHARACTERS

11 . . . specimen testing automation system
12 . . . main conveyor line
13 . . . emergency passing line
14, 15 . . . branch line
16, 17 . . . empty holder conveyor line
18 . . . return line
19 . . . tray
21 . . . driving pulley
22 . . . driven pulley
23 . . . tail pulley
24 . . . belt
25 . . . holder guide rail 26 . . . meandering prevention pulley
27 . . . meandering prevention plate
31 . . . test tube holder
101 . . . host computer

The invention claimed is:

1. A sample conveyor apparatus comprising:
two or more conveyor paths provided along a conveyor route, the two or more conveyor paths being disposed to form a predetermined angle;
a belt used in common by the conveyor paths;
a driving source which drives the belt, thereby conveying at least one of a sample, a sample holder, and a sample rack on the belt as a conveyance object along the conveyor route including across a connection between the conveyor paths; and
a plurality of driven pulleys including a first driven pulley and a second driven pulley disposed at the connection between first and second ones of the conveyor paths, the first driven pulley being in contact with the belt extending from the first one of the conveyor paths and the second driven pulley being in contact with the belt extending to the second one of the conveyor paths, wherein at least one of the first and second driven pulleys is movable to adjust an angle of the belt at the connection between the first and second conveyor paths, and
wherein a distance between the first driven pulley and the second driven pulley is less than or equal to half of a length of the conveyance object in a conveyance direction of the belt.

2. The sample conveyor apparatus according to claim 1, wherein each of the first and second conveyor paths has guides disposed along both sides of the conveyor belt, which prevent the conveyance object being conveyed from falling down.

3. The sample conveyor apparatus according to claim 1, wherein the first one of the conveyor paths is disposed horizontally and the second one of the conveyor paths is disposed inclined at the predetermined angle with respect to a belt surface of the first one of the conveyor paths.

4. The sample conveyor apparatus according to claim 1, wherein the driving source is a driving pulley, and the driven pulleys are dependently driven by the belt driven by the driving pulley, and
wherein tension of the belt can be adjusted by adjusting a position of the driving pulley or the driven pulleys.

5. The sample conveyor apparatus according to claim 1, further comprising:
a meander prevention pulley or plate to adjust imbalance of the belt with respect to the conveyor paths.

6. An automated specimen testing system comprising:
a first conveyor line which conveys a holder or rack having a specimen mounted thereon;
a second conveyor line which conveys the holder or rack having no specimen mounted thereon, and the second conveyor line is provided on a plane different from the first conveyor line; and
a third conveyor line which conveys the holder or rack mutually between the first conveyor line and the second conveyor line,
wherein the third conveyor line includes:
two or more conveyor paths provided along a conveyor route of the third conveyor and disposed to form a predetermined angle,
a belt used in common by the conveyor paths,
a driving source which drives the belt, thereby conveying the holder or rack along the conveyor route including across a connection between the conveyor paths, and
a plurality of driven pulleys including a first driven pulley and a second driven pulley disposed at the connection between first and second ones of the conveyor paths, the first driven pulley being in contact with the belt extending from a first one of the conveyor paths and the second driven pulley being in contact with the belt extending to a second one of the conveyor paths, wherein at least one of the first and second driven pulleys is movable to adjust an angle of the belt at the connection between the first and second conveyor paths, and
wherein a distance between the first driven pulley and the second driven pulley is less than or equal to half of a length of the holder or rack in a conveyance direction of the belt.

7. The automated specimen testing system according to claim 6,
wherein each of the first and second conveyor paths has guides, which prevent the holder or the rack being conveyed from falling down, on both sides thereof.

8. The automated specimen testing system according to claim 6,
wherein the first conveyor line is provided above the second conveyor line,
wherein the first one of the conveyor paths is disposed substantially horizontally and the second one of the conveyor paths is disposed inclined at the predetermined angle with respect to the first one of the conveyor paths.

* * * * *